United States Patent [19]

Gunkel et al.

[11] Patent Number: 4,897,502

[45] Date of Patent: Jan. 30, 1990

[54] PROCESS FOR MAKING SOLID POLYHALOTRIARYL PHOSPHATE ESTERS

[75] Inventors: Louis T. Gunkel, Yardley, Pa.; John Crosby, Lawrenceville, N.J.

[73] Assignee: FMC Corporation, Philadelphia, Pa.

[21] Appl. No.: 105,776

[22] Filed: Oct. 7, 1987

Related U.S. Application Data

[63] Continuation-in-part of Ser. No. 12,417, Feb. 9, 1987, abandoned.

[51] Int. Cl.$^4$ ................................................ C07F 9/09
[52] U.S. Cl. ...................................... 558/102; 558/150
[58] Field of Search ................................. 558/102, 150

[56] References Cited

U.S. PATENT DOCUMENTS

| | | | |
|---|---|---|---|
| 1,866,852 | 7/1932 | Hand et al. | 558/146 |
| 2,561,493 | 7/1951 | Caprio et al. | 558/212 |
| 2,894,015 | 7/1959 | Kyker | 558/152 |
| 3,436,441 | 4/1969 | Thompson | 558/211 |
| 3,526,681 | 9/1970 | English | 558/150 |

FOREIGN PATENT DOCUMENTS

| | | |
|---|---|---|
| 0596592 | 2/1978 | U.S.S.R. |
| 1175937 | 8/1985 | U.S.S.R. |
| 1168819 | 10/1969 | United Kingdom |

OTHER PUBLICATIONS

Kirk–Othmer, "Encyclopedia of Chemical Technology", 3rd Ed., vol. 14, John Wiley & Sons, N.Y., (1981), p. 632.

Barton, A. F., CRC Handbook of Solubility Parameters and Other Cohesion Parameters, CRC Press Inc., Boca Raton, (1985), pp. 94–109.

Translation of Japanese Kokai 50-47953, 4/23/75.

*Primary Examiner*—Jacqueline V. Howard
*Assistant Examiner*—Margaret B. Medley
*Attorney, Agent, or Firm*—R. E. Elden; R. L. Anderson

[57] ABSTRACT

A process is provided for making halogen-substituted triaryl phosphate esters which are normally solid under ambient conditions. The process comprises reacting a halogenated phenol with phosphorus oxychloride in the presence of a magnesium chloride catalyst above the melting point of the desired product. After the reaction is complete the product is recovered by adding an alcohol, such as, pentanol, 2-ethyl hexanol or hexanol and cooling the resulting mixture below the melting point of the product.

12 Claims, No Drawings

PROCESS FOR MAKING SOLID POLYHALOTRIARYL PHOSPHATE ESTERS

This application is a continuation-in-part of copending application Ser. No. 012,417 filed Feb. 9, 1987, now abandoned.

The present invention relates to processes for making halogen-substituted triaryl phosphate esters which are normally solids under ambient conditions. More particularly, the invention relates to a process for making polyhalotriphenyl phosphate esters by the reaction of phosphorus oxychloride and the corresponding polyhalophenol, particularly the reaction of a polybromophenol to make a polybromophenyl phosphate ester.

The reaction of phosphorus oxychloride with a phenolic compound, such as phenol, alkylphenols or halophenols is a well known method for producing triaryl phosphate esters which are useful as flame retardants in plastics. The process is commonly known as phosphorylation. Usually an anhydrous metal chloride catalyst is employed such as aluminum chloride or magnesium chloride. When the product is a triarylphosphate, which is liquid under ambient conditions, the product is usually recovered from the crude reaction mixture by distilling off low boiling components, such as phenols. Subsequently, the desired phosphate ester is recovered by distillation leaving, as a residue, most of the catalyst, color bodies and high-boiling by-products. The crude product may be further refined to remove traces of catalyst and color bodies.

A phosphate ester which is normally a solid under ambient conditions cannot be distilled effectively in this manner, and consequently the product usually contains relatively high concentrations of catalyst residue. These metal halide residues are undesirable in the product in that they are available to catalyze undesired reactions when compounded into the plastic or in an intermediate formulation.

Japanese Patent No. 50-47953 teaches a phosphorylation process in which halophenols and phosphorus oxychloride are reacted at elevated temperatures in the presence of anhydrous metal chlorides such as aluminum, magnesium, iron or boron chlorides, the anhydrous metal chloride being present in an amount of at least 0.05% by weight based on the halophenol. The reference teaches recovering the product by cooling the reaction mixture and adding methanol. The crude product is washed and dried. This process has been found to have a disadvantage of leaving relatively high concentrations of the metal chloride catalyst in the final product.

Triaryl phosphate esters, and polyhalotriaryl phosphate esters are useful as flame retardant additives for plastics. Polyhalotriphenyl phosphate esters are particularly effective flame retardant additives for plastics.

When the triaryl phosphate ester is a solid under ambient conditions, the crude product usually is purified by recrystallization from an aromatic solvent such as toluene or xylene. Such a process is undesirable because the recrystallization steps are costly and the yield of product is reduced. The process usually necessitates further work up of crude product from the solvent mother liquor.

The present invention is a process for preparing a normally solid polyhalotriphenyl phosphate with the formula $(X_nArO)_3P=O$, in which each X is a halogen selected from the group consisting of chlorine and bromine, ArO is a phenoxy group, n is an integer in the range of from 1 to 5, and the ratio of X to P is in the range of from 3 to 10. The process comprises the steps of (a) incorporating into a reaction mixture approximately stoichiometric quantities of phosphorus oxychloride, and a halophenol of the formula $X_nArOH$, in which ArO, X and n are as defined above, and a catalytic quantity of anhydrous magnesium chloride, and (b) heating the reaction mixture to maintain the temperature of the reaction mixture above the temperature at which the polyhalotriphenyl phosphate will separate from the solution as a solid phase. The reaction mixture is maintained at such a temperature for a sufficient time to react substantially all of the phosphorus oxychloride. The product is next separated from the reaction mixture by (c) incorporating a solvent amount of a substantially inert alcohol into the reaction mixture to form an alcohol solution, the alcohol having a Hildebrand solubility parameter $\delta_t$, of at least 20 and less than 23 SI units, and a Hansen dispersion component of between 14.2 and 15.5 units, (d) cooling alcoholic solution sufficiently to form a solid phase in the alcoholic solution, and (e) separating the solid phase from the cooled alcoholic solution. For the purpose of this invention a substantially inert alcohol is one which does not react appreciably with the reaction mixture under the conditions employed.

The concept of the Hildebrand solubility parameter $\delta_t$ is a well known method for expressing the solubility of organic compounds in quantitative terms. The Hildebrand solubility parameter is easily available. It can be either calculated from the heat of vaporization or can be estimated by known methods. In addition, tables listing the Hildebrand solubility parameter (and the Hansen dispersion parameters) for many organic compounds are readily available. For example, Barton, *CRC Handbook of Solubility Parameters and Other Cohesion Parameters*, CRC Press Inc., Boca Raton (1983), pages 94 to 109.

The Hansen parameters $\delta_d$, the dispersion component, $\delta_p$, the polar component and $\delta_h$, the hydrogen-bonding bonding component are also well known. They are related to the solubility parameter $\delta_t$ as follows:

$$\delta_t^2 = \delta_d^2 + \delta_p^2 + \delta_{h2}$$

Unexpectedly, it has been found that an alcohol having a solubility parameter of at least 20 and less than 23 SI units and a Hansen dispersion component of between 14.2 and 15.5 SI units will not only be effective in separating a normally solid polyhalotriphenyl phosphate product from the phosphorylation mother liquor but also appears to prevent codeposition of magnesium chloride with the product. A C5 to C8 alcohol is preferred.

It is well known that 15.5 g magnesium chloride will dissolve in 100 g methanol at 0° C., and that only 3.61 g magnesium chloride will dissolve in 100 g ethanol at the same temperature. Consequently, it is wholly unexpected to find that pentanol, hexanol or other alcohols of the present invention are superior to methanol in reducing the magnesium chloride in the solid ester product.

Japanese Patent No. 50-47953 also teaches that when less than 0.1% by weight of metal halide catalyst is used based on the halophenol, that the yield of the polyhalotriaryl phosphate ester decreases and that the minimum effective amount of catalyst is 0.05% by weight. Surprisingly, the process of the present invention provides 90% yields employing only 0.02% magnesium chloride.

On the other hand, operating without catalyst requires an excessively high temperature of at least 260° C. and requires a long time to complete the reaction. The combination of the high temperature and long reaction time results in excessive degradation of the product.

Any inert alcohol may be employed which has a Hildebrand solubility parameter of at least 20 and less than 23 and a Hansen dispersion component of between 14.2 and 15.5. Preferred alcohols include pentanol, hexanol, and 2-ethylhexanol. Pentanol is especially preferred as an organic liquid. Table I lists the Hildebrand solubility parameter ($\delta_t$) and Hansen dispersion coefficient for a number of organic liquids suitable for the present invention.

TABLE I

| Liquid | Hildebrand Solubility Parameter SI | Hansen Dispersion Component SI |
|---|---|---|
| 1-hexanol | 22.0 | 15.0 |
| 2-butanol | 22.7 | 14.5 |
| 1-pentanol | 22.7 | 14.4 |
| 2-ethylhexanol | 20.8 | 15.1 |
| 2-pentanol | 22.2 | 15.0 |
| amyl alcohol (pract.) | 22.0 | 14.5 |
| 1-decanol | 20.5 | 15.4 |
| 1-heptanol | 21.5 | 15.1 |
| 2-heptanol | 20.1 | 14.6 |
| 3-heptanol | 20.2 | 14.6 |
| 1-octanol | 21.1 | 15.2 |

The temperature of the reaction mixture should be maintained sufficiently high to prevent precipitation or crystallization of a reaction product. Generally it is convenient to maintain the temperature at or above the normal melting point of the desired product. Temperatures higher than the melting point not only increase the reaction rate but also increase the formation of color bodies. It is generally desirable to maintain the temperature of the reaction mixture under 200° C. Preferably the temperature of the reaction mixture is maintained between the melting point of the desired product and 180° C., more preferably between 130° C. and 180° C.

The best mode of practicing the present invention may be determined by one skilled in the art from the following nonlimiting examples.

COMPARATIVE EXAMPLE A

Phosphorylation of 2,4-dibromophenol with POCl$_3$ without catalyst.

A 22 liter flask equipped with stirrer, reflux condenser, thermometer, and additional funnel containing 23,330 g of 2,4-dibromophenol was heated to 180° C. and 5,031 g of phosphorus oxychloride were added to the dibromophenol over 4 hours. Heat was then applied to the flask to raise the temperature to 265° C. It was necessary to continue the reaction for 52 hours after the POCl$_3$ was added to completely react all of it. The reaction was followed by gas chromatographic analysis and the run was considered complete when all of the phosphorochloridates had disappeared.

The material was worked up by cooling the hot crude reaction mixture to 110° C. and adding it to 10 liters of toluene in which it is very soluble. This mixture was cooled with an ice bath and the product crystallized out. The filtered solid product still contained 0.5% 2,4-dibromophenol (DBP) and had to be washed twice with methanol (solubility parameter 14.5, Hansen dispersion component 7.4) to reduce the phenol level below 0.2%. The yield of recovered product was 17,887 g or about 68% based on POCl$_3$ charged. Considerable product remained in the toluene filtrate. The product was gritty.

EXAMPLE 1

Magnesium chloride catalyst at a low temperature 300 g of 2,4-dibromophenol (DBP) and 0.13 g (0.04% based on the bromophenol) of anhydrous magnesium chloride were charged into a 500 ml three necked round bottom flask equipped with thermometer, stirrer, reflux condenser and addition funnel. The mixture was heated to 120° C. and 64.0 g of phosphorus oxychloride (POCl$_3$) were added over a one hour period. The temperature was then raised to 180° C. and the reaction was analyzed by gas chromatography (GC) until all of the POCl$_3$ was reacted. The final analysis of the reaction showed 0.8% DBP, 0.3% chloridate, and 98.9% ester product.

The run was cooled to 130° C. and added to 400 ml of 1-pentanol. This mixture precipitated out product as soon as the temperature reached the freezing point of the DBP (110° C.). At 30° C., the product was filtered from the 1-pentanol mother liquor. The pentanol solution contained 0.2% DBP, 0.1% chloridates and 0.4% product. The product showed 0.2% each of DBP and chloridate and 99.6% tris(2,4-dibromophenyl) phosphate. The calculated amount of magnesium in the product based on the MgCl$_2$ charge was 110 ppm. The amount determined in the product by analysis was 12 ppm. The pentanol mother liquor contained 97 ppm magnesium, demonstrating that the process does remove the magnesium residues. The product was a white free-flowing powder with a melting point of 101.4° C.

COMPARATIVE EXAMPLE B

Aluminum Chloride Catalyst At A Low Temperature 300 g of 2,4-dibromophenol and 0.13 g (0.04% based on the bromophenol) of anhydrous aluminum chloride were charged to a 500 ml three necked round bottom flask equipped with thermometer, stirrer, reflux condenser and addition funnel. The mixture was heated to 120° C. and 64.0 g of phosphorus oxychloride (POCL$_3$) were added over a one hour period. The temperature was then raised to 180° C. and the reaction was analyzed by GC until all of the POCl$_3$ was reacted.

The run was cooled to 130° C. and added to 400 ml of 1-pentanol. This mixture precipitated out product as soon as the temperature reached 110° C. At 30° C. the product was filtered from the pentanol mother liquor. The dry weight of the product was 272 g. The product was a white, free-flowing granular powder which analyzed over 99% tris(2,4-dibromophenyl) phosphate. The melting point was 101.6° C. and the aluminum content was 60 ppm (theory=95 ppm). The mother liquor contained only 15 ppm of aluminum.

EXAMPLE 2

A large scale example using MgCl$_2$ as catalyst and low temperature.

3,146 g of 2,4-dibromophenol and 0.73 g of anhydrous magnesium chloride (0.023%) were charged to a 5 liter three necked, round bottomed flask equipped with thermometer, stirrer, condenser and addition funnel. 673 g of POCl₃ were then added to the pot contents at 120° C. over a one hour period. The reaction temperature was then raised to 180° C. over a one hour period and held there for 3 hours until the reaction was complete as evidenced by the fact that the POCl₃ was completely consumed and there were no longer any chloridates remaining in the reaction mixture. After the reaction the pot showed 0.33% DBP, a trace of chloridates (0.1–0.2) and 98.5% tris(2,4-dibromophenyl) phosphate.

The crude reaction product was cooled to 140° C. and added to 5 liters of pentanol. The white solids that precipitated were filtered and dried at 80° C. in a vacuum oven overnight. The weight of recovered, dry product was 3,051 g, representing an 87% yield based on POCl₃. The product analyzed greater than 99% by GC analysis and had a melting point of 100.1° C. The magnesium level in the product was 4.5 ppm (expected level was 232 ppm).

EXAMPLE 3

Hexanol As The Organic Liquid.

300 g of 2,4-dibromophenol and 0.07 g (0.02% based on the bromophenol) of anhydrous magnesium chloride were charged to a 500 ml three necked round bottom flask equipped with thermometer, stirrer, reflux condenser and addition funnel. The mixture was heated to 120° C. and 64.0 g of phosphorus oxychloride (POCl₃) were added over a one hour period. The temperature was then raised to 180° C. and the reaction was analyzed by GC until all of the POCl₃ was reacted (4 hours).

The final analysis of the reaction showed 1.0% DBP, 0.6% chloridate, and 98.4% ester product.

The run was cooled to 130° C. and added to 400 ml of 1-hexanol. This mixture precipitated out product as soon as the temperature reached the freezing point of the DBP (110° C.). At 30° C. the product was filtered from the 1-hexanol mother liquor. The hexanol solution contained 0.2% DBP, 0.3% chloridates and 0.4% product. The product showed 0.2% of DBP and no chloridate. The product concentration was 99.+%.

The amount of magnesium calculated to be in the product based on the MgCl₂ charge was 110 ppm. The amount determined in the product by analysis was 8.0 ppm, demonstrating that hexanol is also useful in removing magnesium catalyst residues from the product. The product was a white free-flowing powder with a melting point of 100.6° C.

EXAMPLE 4

A comparison between 2-propanol and 2-ethylhexanol as the organic liquid.

300 g of 2,4-dibromophenol and 0.13 g (0.04% based on the bromophenol) of anhydrous magnesium chloride were charged to a 500 ml three necked round bottom flask equipped with thermometer, stirrer, reflux condenser and addition funnel. The mixture was heated to 120° C. and 64.0 g of phosphorus oxychloride (POCl₃) were added over a one hour period. The temperature was then raised to 180° C. and the reaction was analyzed by GC until all of the POCl₃ was reacted (4 hours).

The final analysis of the reaction showed 1.6% DBP, 0.3% chloridate, and 95.0% ester product.

The crude product was worked up by pouring a portion into 2-ethylhexanol and the remainder into 2-propanol (solubility parameter 12.0, Hansen dispersion component 7.6). The tris(2,4-dibromophenyl) phosphate was precipitated from both alcohols. The expected amount of magnesium in the product was 108 ppm. The magnesium found in the 2-propanol sample was 100 ppm and that in the 2-ethylhexanol batch was 12 ppm.

EXAMPLE 5

Tris(4-bromophenyl) phosphate 200 g of 4-bromophenol (1.15 moles) and 0.21 g of anhydrous magnesium chloride were charged to a 500 ml three necked round bottomed flask equipped with thermometer, stirrer, reflux condenser and addition funnel. The mixture was heated to 120° C. and 60 g (1.17) of phosphorus oxychloride (POCl₃) were added over a 30 minute period. The temperature was then raised to 180° C. and the reaction mixture was held at this temperature and analyzed by gas chromatograph until it was determined that all of the POCl₃ had been reacted (2 hours). The final analysis showed 0.8% 4-bromophenol and 99.0% ester product in the reaction mixture.

The crude product was worked up by cooling it to 150° C. and adding it to 400 ml of 1-pentanol and then cooling this mixture to 25° C. The product precipitated out, was filtered and dried under vacuum at 80° C.

The pentanol mother liquor contained 0.24% 4-bromophenol, no chloridates and 0.52% ester product. The magnesium content of the pentanol was 190 ppm.

The product, tris(4-bromophenol) phosphate ester contained no detectable 4-bromophenol or chloridates. The product had a dry weight of 200.5 g corresponding to a 91% yield of material.

The ester product was a white, free-flowing powder with a melting point of 102–105° C. The magnesium content in the product was 2.4 ppm.

I claim:

1. A process for preparing a normally solid polyhalotriphenyl phosphate with the formula $(X_nAro)_3P=O$, in which each X is a halogen selected from the group consisting of chlorine and bromine, ArO is a phenoxy group, n is an integer in the range of from 1 to 5, and the ratio of X to P is in the range of from 3 to 10, comprising:

(a) incorporating into a reaction mixture approximately stoichiometric quantities of phosphorous oxychloride, and a halophenol of the formula $X_nArOH$, in which ArO, X and n are as defined above, and a catalytic quantity of anhydrous magnesium chloride, (b) heating the reaction mixture to maintain the temperature of the reaction mixture above the temperature at which the polyhalotriphenyl phosphate will separate from the solution as a solid phase for a sufficient time to react substantially all of the phosphorous oxychloride, (c) incorporating a solvent amount of a substantially inert alcohol into the reaction mixture to form an alcoholic solution, the alcohol having a Hildebrand solubility parameter $\delta_t$ of at least 20 and less than 23 SI units, and a Hansen dispersion component of between 14.2 and 15.5 SI units, (d) cooling the alcoholic solution sufficiently to form a solid phase in the alcoholic solution, and (e) separating the solid phase from the cooled alcoholic solution, said solid phase comprising the polyhalotriphenyl phosphate with a substantially reduced quantity of magnesium.

2. The process of claim 1 wherein the alcohol is a C5 to C8 alcohol.

3. The process of claim 1 wherein the halophenol is a brominated phenol.

4. The process of claim 2 wherein the halophenol is a brominated phenol.

5. The process of claim 1 wherein the reaction mixture is maintained at a temperature between the melting point of the desired polyhalotriphenyl phosphate and 200° C.

6. The process of claim 2 wherein the reaction mixture is maintained at a temperature between the melting point of the desired polyhalotriphenyl phosphate and 200° C.

7. The process of claim 3 wherein the reaction mixture is maintained at a temperature between the melting point of the desired polyhalotriphenyl phosphate and 200° C.

8. The process of claim 4 wherein the reaction mixture is maintained at a temperature between the melting point of the desired polyhalotriphenyl phosphate and 200° C.

9. A process for preparing a polybromotriphenyl phosphate with the formula $(Br_nArO)_3P=O$ in which ArO is a phenyl group, n is an integer in the range of from 1 to 5, and the ratio of Br to P is in the range of from 3 to 10, comprising:

(a) incorporation into a reaction mixture approximately stoichiometric quantities of phosphorous oxychloride, and a bromophenol of the formula $Br_nArOH$, in which ArO and n are as defined above, and a catalytic quantity of anhydrous magnesium chloride, (b) heating the reaction mixture to maintain the temperature of the reaction mixture above the temperature at which the polybromotriphenyl phosphate will separate from the solution as a solid phase for a sufficient time to react substantially all of the phosphorous oxychloride, (c) incorporating a solvent amount of a C5 to C8 inert alcohol into the reaction mixture to form an alcoholic solution, (d) cooling the alcoholic solution sufficiently to form a solid phase in the alcoholic solution, and (e) separating the solid phase from the cooled alcoholic solution, said solid phase comprising the polyhalootriphenyl phosphate with a substantially reduced quantity of magnesium.

10. The process of claim 9 wherein the homophenol is 2,4-dibromophenol and the polybromotriphenyl phosphate is tris(2,4-dibromophenyl) phosphate.

11. The process of claim 9 wherein the temperature of the reaction mixture is maintained between 130° C. and 180° C.

12. The process of claim 10 wherein the temperature of the reaction mixture is maintained between 130° C. and 108° C.

* * * * *